United States Patent
Bon Betemps et al.

(10) Patent No.: US 9,402,799 B2
(45) Date of Patent: Aug. 2, 2016

(54) STERILIZED COMPOSITION COMPRISING AT LEAST ONE HYALURONIC ACID AND MAGNESIUM ASCORBYL PHOSPHATE

(71) Applicant: LABORATOIRES VIVACY, Archamps (FR)

(72) Inventors: Jeremie Bon Betemps, Albens (FR); Estelle Piron, Saint Etienne de Cuines (FR)

(73) Assignee: LABORATORIES VIVACY, Archamps (FR)

( * ) Notice: Subject to any disclaimer, the term of this patent is extended or adjusted under 35 U.S.C. 154(b) by 110 days.

(21) Appl. No.: 14/013,374

(22) Filed: Aug. 29, 2013

(65) Prior Publication Data

US 2014/0088037 A1 Mar. 27, 2014

Related U.S. Application Data

(60) Provisional application No. 61/694,527, filed on Aug. 29, 2012.

(30) Foreign Application Priority Data

Aug. 29, 2012 (FR) .................... 12 58082

(51) Int. Cl.
| | | |
|---|---|---|
| A61K 8/73 | (2006.01) | |
| A61K 8/55 | (2006.01) | |
| C08B 37/08 | (2006.01) | |
| A61K 8/44 | (2006.01) | |
| A61L 27/52 | (2006.01) | |
| A61L 27/20 | (2006.01) | |
| A61Q 19/08 | (2006.01) | |
| A61L 27/54 | (2006.01) | |
| A61K 8/67 | (2006.01) | |
| A61K 8/46 | (2006.01) | |
| C08L 5/08 | (2006.01) | |
| C08K 5/41 | (2006.01) | |
| C08K 5/529 | (2006.01) | |

(52) U.S. Cl.
CPC ............... *A61K 8/735* (2013.01); *A61K 8/447* (2013.01); *A61K 8/46* (2013.01); *A61K 8/55* (2013.01); *A61K 8/676* (2013.01); *A61L 27/20* (2013.01); *A61L 27/52* (2013.01); *A61L 27/54* (2013.01); *A61Q 19/08* (2013.01); *C08B 37/0072* (2013.01); *C08L 5/08* (2013.01); *A61K 2800/91* (2013.01); *A61L 2300/428* (2013.01); *A61L 2400/06* (2013.01); *A61L 2430/34* (2013.01); *C08K 5/41* (2013.01); *C08K 5/529* (2013.01)

(58) Field of Classification Search
CPC ......... A61K 8/735; A61K 8/447; A61K 8/55; C08B 37/0072; A61L 27/52; A61L 27/20; A61Q 19/08
See application file for complete search history.

(56) References Cited

U.S. PATENT DOCUMENTS

| | | | |
|---|---|---|---|
| 5,801,192 A | 9/1998 | Dumas et al. | |
| 6,184,247 B1 | 2/2001 | Schneider | |
| 2006/0194758 A1 | 8/2006 | Lebreton | |
| 2007/0237816 A1* | 10/2007 | Finkelstein | ................... 424/464 |
| 2010/0184720 A1 | 7/2010 | Gavard Molliard et al. | |
| 2010/0303873 A1 | 12/2010 | Piron et al. | |
| 2011/0172180 A1* | 7/2011 | Gousse | .................. A61K 8/735 |
| | | | 514/54 |
| 2011/0230438 A1 | 9/2011 | Bos | |
| 2013/0172288 A1 | 7/2013 | Bon Betemps et al. | |

FOREIGN PATENT DOCUMENTS

| | | |
|---|---|---|
| CA | 2079205 | 3/1994 |
| CA | 2 519 798 A1 | 12/2004 |
| EP | 1 629 830 A1 | 3/2006 |
| FR | 2 983 483 | 6/2013 |
| GB | 2 228 197 A | 8/1990 |
| WO | WO 91/04058 A2 | 4/1991 |
| WO | WO 93/16732 A1 | 9/1993 |
| WO | WO 93/16733 A1 | 9/1993 |
| WO | WO 94/07505 A1 | 4/1994 |
| WO | WO 95/26193 A1 | 10/1995 |
| WO | WO 95/29683 A1 | 11/1995 |
| WO | WO 95/30423 A2 | 11/1995 |
| WO | WO 96/06622 A1 | 3/1996 |
| WO | WO 96/19099 A2 | 6/1996 |
| WO | WO 98/17320 A1 | 4/1998 |
| WO | WO 99/49878 A1 | 10/1999 |
| WO | WO 00/46253 A1 | 8/2000 |
| WO | WO 00/71094 A1 | 11/2000 |

(Continued)

OTHER PUBLICATIONS

Alleman et al., Clin. Invest. Aging, 2008, 3(4), p. 629-634.*

(Continued)

*Primary Examiner* — Jonathan S Lau
(74) *Attorney, Agent, or Firm* — Oliff PLC

(57) ABSTRACT

The invention relates to a sterilized composition comprising at least one hyaluronic acid or biologically acceptable salt thereof, alone or in a mixture, and magnesium ascorbyl phosphate, in a ratio [HA]/[MAP] by mass of the amount of hyaluronic acid or salt thereof [HA] to the amount of magnesium ascorbyl phosphate [MAP] of greater than or equal to 1, the amount of magnesium ascorbyl phosphate being between 0.001% and 1% by weight, relative to the total weight of said composition, with an elastic component G' which is retained or improved after sterilization and is between 5 and 400 Pa. It also relates to a composition of the invention which further includes dimethyl sulfone, to methods for producing same, and to uses thereof.

23 Claims, 1 Drawing Sheet

(56) References Cited

FOREIGN PATENT DOCUMENTS

| WO | WO 2004/092222 A2 | 10/2004 |
|----|-------------------|---------|
| WO | WO 2004/105720 A1 | 12/2004 |
| WO | WO 2007/077399 A2 | 7/2007 |
| WO | WO 2009/005790 A2 | 1/2009 |
| WO | WO 2009/014559 A2 | 1/2009 |
| WO | WO 2009/024670 A2 | 2/2009 |
| WO | WO 2009/071697 A1 | 6/2009 |
| WO | WO 2011/086458 A1 | 7/2011 |
| WO | WO 2012/104419 A1 | 8/2012 |

OTHER PUBLICATIONS

Ballin et al., Am. J. Clin. Dermatol., 2015, 16(4), p. 271-283.*

* cited by examiner

STERILIZED COMPOSITION COMPRISING AT LEAST ONE HYALURONIC ACID AND MAGNESIUM ASCORBYL PHOSPHATE

Hyaluronic acid has been used for more than a decade and a half in the beauty sector, where it has proved to be harmless and effective. At present, in the market for esthetic filling gels or fillers, the products that are most widely used are gels based on crosslinked hyaluronic acid originating from biofermentation.

The use of biofermentation-derived hyaluronic acid in fields such as the filling in of wrinkles, viscosupplementation, ophthalmic treatment or else the treatment of urinary incontinence is acknowledged and appreciated all the more since, owing to its natural presence in the human body, and more particularly in the dermis, the synovial fluid, and the cornea, the risks posed by the side-effects are minimized.

In order to improve these hyaluronic acid formulations and/or to endow them with particular properties, a number of additives may be added to these formulations.

One of the major drawbacks of adding additives to the formulations is the potential deterioration in their rheological and/or viscoelastic properties or in their stability, whether directly during addition or during sterilization phases, or over time, for example, during storage.

Ascorbic acid, also known as vitamin C, is a powerful antioxidant which is involved in numerous biological processes, such as the synthesis of collagen and the metabolism of certain amino acids. Vitamin C, unfortunately, is unstable in aqueous solutions, and therefore cannot be used in formulations of hyaluronic acid that are formulated in water. Some of its derivatives, the ascorbic acid phosphate ester salts conventionally referred to as ascorbylphosphate salts, are stable in aqueous formulation.

Therefore they can theoretically be incorporated into hyaluronic acid formulations.

Dimethyl sulfone is a powerful anti-inflammatory which inhibits the allergic response caused by xenobiotics, which is capable of protecting both keratinocytes and fibroblasts from the adverse effect of ultraviolet radiation, and which inhibits the action of cytokines.

The incorporation of dimethyl sulfone is therefore also advantageous to contemplate in formulations intended for filling in wrinkles or for viscosupplementation.

Many compositions comprising hyaluronic acid and an ascorbyl phosphate salt have been described, especially cosmetic compositions such as, for example, the compositions described in patent application WO1996/19099 to LVMH or in patent application GB 2 228 197 to CHISSO Corporation, but for the most part these compositions are compositions in which hyaluronic acid is not the major constituent, the ratio of the amount of hyaluronic acid to the amount of ascorbyl phosphate salt is generally less than 1. Furthermore, they are intended for topical use and not for viscosupplementation or for filling, and are consequently not subjected to sterilizing operations.

Other compositions are also described in WO2000/71094 to AMWAY Corporation, these compositions exhibiting the same characteristics as the formulations described in the abovementioned patent applications, and these compositions, although confirming the interest of ascorbyl phosphate salts, do not teach the possibility of formulating products for filling or for viscosupplementation in which the major constituent is hyaluronic acid with an ascorbyl phosphate salt.

But in patent application WO2011/086458 to ALLERGAN, compositions are described that are intended for filling in wrinkles or for viscosupplementation and that are subjected to sterilization, and they comprise hyaluronic acid and vitamin C derivatives such as ascorbic acid 2-glucoside, sodium ascorbyl phosphate, or else magnesium ascorbyl phosphate, in an amount of between 0.6% and 2% by weight, relative to the weight of the composition.

According to the patentee, the compositions comprising ascorbic acid 2-glucoside provide access to formulations which are stable and whose stability increases—see example 6—as the concentration of ascorbic acid 2-glucoside goes up.

Formulations comprising sodium ascorbyl phosphate at 2%—example 5—are considered to be stable.

But compositions comprising magnesium ascorbyl phosphate in an amount of 2% by weight, relative to the total weight of the composition, are described by the patentee—see example 4—as being unstable after sterilization by steam autoclaving; however, the hyaluronic acid content of said compositions is not disclosed, the [HA]/[MAP] ratios are therefore not amenable to calculation, and the results are unexploitable and impossible to reproduce.

Patent application WO 2012/104419 to Q-MED describes injectable compositions which are intended for filling in wrinkles or for viscosupplementation and are subjected to sterilization. They comprise hyaluronic acid, a local anesthetic, and an ascorbic acid derivative such as, in particular, sodium ascorbyl phosphate, magnesium ascorbyl phosphate, or else ascorbic acid 2-glucoside, in an amount of between 0.01 and 1 mg/ml.

In these compositions the presence of the ascorbic acid derivative prevents or alleviates the adverse effects of the local anesthetic on the viscosity and/or elasticity of the composition during sterilization. This patent application, indeed, describes substantial increases in the viscosities and in the elastic components G' of the compositions following the addition of the local anesthetic.

This patent application specifies that compositions comprising an ascorbic acid derivative do not have a stability which is improved relative to the same compositions not containing ascorbic acid, and that the addition of ascorbic acid derivatives may give rise to a slight decrease in the stability of the compositions.

Examples show that the addition of magnesium ascorbyl phosphate is able to counter the effect of lidocaine on the elasticity of compositions of crosslinked hyaluronic acid. In this case the elasticity of the composition is reduced following the addition of magnesium ascorbyl phosphate.

Other examples show that the addition of magnesium ascorbyl phosphate is able to counter the effect of lidocaine on the viscosity of noncrosslinked hyaluronic acid compositions. In this case the viscosity of the composition is reduced following the addition of magnesium ascorbyl phosphate.

Patent application WO 2009/005790 to CARBYLAN BIOSURGERY describes compositions used in injectable or implantable formulations that are utilized, for example, in viscosupplementation, or adhesive compositions for biomedical applications. These compositions are subjected to sterilization and comprise hyaluronic acid chemically modified with a substituent containing a thiol function and ascorbic acid or a derivative thereof such as sodium ascorbate or palmitoyl ascorbate.

These compositions comprising modified hyaluronic acid exhibit improved stability.

It has been demonstrated, entirely surprisingly and unexpectedly, in view of the teachings in the prior art described above, that magnesium ascorbyl phosphate, in amounts of less than or equal to 1% in compositions comprising crosslinked hyaluronic acid, improves or retains the rheological characteristic of the elastic component G', relative to compositions comprising crosslinked hyaluronic acid alone, after sterilization.

As demonstrated in the examples, this effect is not observed for compositions comprising sodium ascorbyl phosphate.

The applicant has likewise shown that magnesium ascorbyl phosphate, in amounts of less than or equal to 1% in compositions comprising noncrosslinked hyaluronic acid, makes it possible to retain the viscosities of the compositions after sterilization and improves or retains the rheological characteristic of the elastic component G' relative to compositions comprising noncrosslinked hyaluronic acid alone, after sterilization.

The present invention therefore provides access to compositions comprising hyaluronic acid and a magnesium ascorbyl phosphate salt, with rheological properties that are improved or retained after sterilization.

In one embodiment, when the hyaluronic acid is crosslinked, the compositions according to the invention exhibit values for rheological characteristics that are improved after sterilization, relative to the compositions not containing a magnesium ascorbyl phosphate salt.

The present invention provides a composition comprising at least one hyaluronic acid or salt thereof, alone or in a mixture, which is crosslinked or noncrosslinked, and an ascorbyl phosphate salt; methods for producing said composition; and the use thereof to formulate a composition for filling in wrinkles, or a viscosupplementation composition.

The present invention provides a sterilized composition comprising at least one hyaluronic acid or biologically acceptable salt thereof, alone or in a mixture, and magnesium ascorbyl phosphate, in a ratio [HA]/[MAP] by mass of the amount of hyaluronic acid or salt thereof [HA] to the amount of magnesium ascorbyl phosphate [MAP] of greater than or equal to 1, the amount of magnesium ascorbyl phosphate being between 0.001% and 1% by weight, relative to the total weight of said composition, with an elastic component G' which is retained or improved after sterilization and is between 5 and 400 Pa.

In one embodiment, the elastic component G' is retained or improved after sterilization and is between 5 and 350 Pa.

In one embodiment, the elastic component G' is retained or improved after sterilization and is between 50 and 300 Pa.

In one embodiment, the composition is sterilized by steam autoclaving.

In one embodiment, the composition is sterilized by ethylene oxide.

In one embodiment, the composition is sterilized by irradiation with gamma rays γ.

By hyaluronic acid or a biologically acceptable salt thereof, alone or in a mixture, is meant hyaluronic acid, crosslinked or noncrosslinked, alone or in a mixture, optionally modified chemically by substitution, alone or in a mixture.

In one embodiment, the composition according to the invention comprises at least one noncrosslinked hyaluronic acid or salt thereof, alone or in a mixture.

In one embodiment, the composition according to the invention comprises at least one crosslinked hyaluronic acid or salt thereof, alone or in a mixture.

In one embodiment, the composition according to the invention comprises at least one co-crosslinked hyaluronic acid or salt thereof, alone or in a mixture.

In one embodiment, the composition according to the invention comprises at least one hyaluronic acid modified chemically by substitution or salt thereof, alone or in a mixture.

In one embodiment, the hyaluronic acid is in the form of a sodium or potassium salt.

In one embodiment, the composition according to the invention has a ratio [HA]/[MAP] by mass of the amount of hyaluronic acid or salt thereof [HA] to the amount of magnesium ascorbyl phosphate [MAP] of between 10 and 30.

In one embodiment, the composition according to the invention has a ratio [HA]/[MAP] by mass of the amount of hyaluronic acid or salt thereof [HA] to the amount of magnesium ascorbyl phosphate [MAP] of between 15 and 25.

In one embodiment, the composition according to the invention has a ratio [HA]/[MAP] by mass of the amount of hyaluronic acid or salt thereof [HA] to the amount of magnesium ascorbyl phosphate [MAP] of approximately 20.

In one embodiment, the composition according to the invention has a magnesium ascorbyl phosphate content of between 0.01% and 0.5% by weight, relative to the total weight of the composition.

In one embodiment, the composition according to the invention has a magnesium ascorbyl phosphate content of between 0.03% and 1% by weight, relative to the total weight of the composition.

In one embodiment, the composition according to the invention has a magnesium ascorbyl phosphate content of between 0.05% and 0.15% by weight, relative to the total weight of the composition.

In one embodiment, the composition according to the invention has a magnesium ascorbyl phosphate content of between 0.03% and 0.1% by weight, relative to the total weight of the composition.

In one embodiment, the composition according to the invention has a magnesium ascorbyl phosphate content of between 0.07% and 0.1% by weight, relative to the total weight of the composition.

In one embodiment, the composition according to the invention has a magnesium ascorbyl phosphate content of between 0.01 and 10 mg/g of composition.

In one embodiment, the composition according to the invention has a magnesium ascorbyl phosphate content of between 0.3 and 10 mg/g of composition.

In one embodiment, the composition according to the invention has a magnesium ascorbyl phosphate content of between 0.1 and 5 mg/g of composition.

In one embodiment, the composition according to the invention has a magnesium ascorbyl phosphate content of between 0.5 and 1.5 mg/g of composition.

In one embodiment, the composition according to the invention has a magnesium ascorbyl phosphate content of between 0.3 and 1 mg/g of composition.

In one embodiment, the composition according to the invention has a magnesium ascorbyl phosphate content of between 0.7 and 1 mg/g of composition.

Mw or "molecular mass" refers to the mass-average molecular mass of the polymers, measured in daltons.

In one embodiment, the composition according to the invention is characterized in that the molecular mass Mw of the hyaluronic acid or salt thereof is in a range of 0.01 MDa to 5 MDa.

In one embodiment, the composition according to the invention is characterized in that the molecular mass Mw of the hyaluronic acid or salt thereof is in a range of 0.1 MDa to 3.5 MDa.

In one embodiment, the composition according to the invention has a total content of hyaluronic acid or salt thereof of between 0.2% and 5% by weight, relative to the total weight of said composition.

In one embodiment, the composition according to the invention has a total content of hyaluronic acid or salt thereof of greater than or equal to 1% by weight, relative to the total weight of said composition.

In one embodiment, the composition according to the invention has a total content of hyaluronic acid or salt thereof of between 2 mg/g and 50 mg/g of composition.

In one embodiment, the composition according to the invention has a total content of hyaluronic acid or salt thereof of between 4 mg/g and 40 mg/g of composition.

In one embodiment, the composition according to the invention has a total content of hyaluronic acid or salt thereof of between 5 mg/g and 30 mg/g of said composition.

In one embodiment, the composition according to the invention has a total content of hyaluronic acid or salt thereof of between 10 mg/g and 30 mg/g of said composition.

In one embodiment, the composition according to the invention comprises at least one noncrosslinked hyaluronic acid or salt thereof.

In one embodiment, the composition according to the invention comprises at least one crosslinked hyaluronic acid or salt thereof.

In the present invention the degree of crosslinking, X, is defined as being equal to the following ratio:

$$x = \frac{\left(\begin{array}{c}\text{number of moles of crosslinker}\\ \text{introduced into the reaction mixture}\end{array}\right)}{\left(\begin{array}{c}\text{number of moles of disaccharide}\\ \text{unit introduced into the reaction mixture}\end{array}\right)}$$

In one embodiment, the crosslinked hyaluronic acid has a degree of crosslinking X of between 0.001 and 0.5.

In one embodiment, the crosslinked hyaluronic acid has a degree of crosslinking X of between 0.01 and 0.25.

In one embodiment, the crosslinked hyaluronic acid has a degree of crosslinking X of between 0.1 and 0.2.

In one embodiment, the hyaluronic acid is co-crosslinked as described in patent application WO2000/046253.

In one embodiment, the composition according to the invention comprises a mixture of crosslinked and non-crosslinked hyaluronic acids or salts thereof.

In one embodiment, the composition according to the invention comprises a mixture of crosslinked hyaluronic acids or salts thereof.

In one embodiment, the mixture of crosslinked hyaluronic acids or salts thereof is a single-phase mixture of the type described in patent application WO2009/071697.

In one embodiment, the mixture of crosslinked hyaluronic acids or salts thereof is a mixture obtained by mixing a number of hyaluronic acids or salts thereof with different molecular masses prior to their crosslinking, as described in patent application WO2004/092222.

In one embodiment, the composition according to the invention comprises at least one hyaluronic acid or salt thereof which is substituted by a group imparting lipophilic or hydrating properties, such as, for example, substituted hyaluronic acids as described in patent application FR 1161125 in the name of the applicant.

In one embodiment, the composition further comprises another polysaccharide.

In one embodiment, this other polysaccharide is selected from the group consisting of cellulose, alginic acid, or a salt thereof.

In one embodiment, the composition according to the invention further comprises dimethyl sulfone.

In one embodiment, the composition according to the invention has a dimethyl sulfone content of between 0.001% and 5% by weight, relative to the total weight of said composition.

In one embodiment, the composition according to the invention has a dimethyl sulfone content of between 0.1% and 1% by weight, relative to the total weight of said composition.

In one embodiment, the composition according to the invention has a dimethyl sulfone content of between 0.1 and 20 mg/g of composition.

In one embodiment, the composition according to the invention has a dimethyl sulfone content of between 1 and 10 mg/g of composition.

In one embodiment, the composition according to the invention further comprises at least one additional agent.

In one embodiment, the composition according to the invention has an additional agent selected from antioxidants and local anesthetics, alone or in a mixture.

In one embodiment, the composition according to the invention has local anesthetics selected from the group consisting of lidocaine, procaine, mepivacaine, ropivacaine, bupivacaine, or pharmaceutically acceptable salts thereof.

In one embodiment, the composition according to the invention has the local anesthetic being lidocaine hydrochloride.

In one embodiment, the composition according to the invention has the antioxidants selected from polyols.

In one embodiment, the composition according to the invention has the antioxidants selected from mannitol and sorbitol, alone or in a mixture.

In one embodiment, the composition according to the invention has the antioxidant being mannitol.

In one embodiment, the composition according to the invention has the antioxidant being sorbitol.

In one embodiment, the composition according to the invention has the antioxidant being a mixture of mannitol and sorbitol.

In one embodiment, the composition according to the invention has an additional agent content of between 0.01% and 10% by weight, relative to the total weight of the composition.

In one embodiment, the composition according to the invention has an additional agent content of between 0.1% and 5% by weight, relative to the total weight of the composition.

In one embodiment, the composition according to the invention has an additional agent content of between 0.1 and 100 mg/g of composition.

In one embodiment, the composition according to the invention has an additional agent content of between 1 and 50 mg/g of composition.

In one embodiment, the invention is a viscosupplementation composition which comprises at least one composition according to the invention.

In one embodiment, the invention is a composition for treating xerophthalmia or ocular dryness and comprises at least one composition according to the invention.

Depending on the embodiments, said compositions are used as artificial tears, lachrymal gels, or lubricants.

In one embodiment, the composition of the invention has its elastic component G' retained or improved after sterilization and is between 5 and 400 Pa.

In one embodiment, the elastic component G' is retained or improved after sterilization and is between 5 and 350 Pa.

In one embodiment, the elastic component G' is retained or improved after sterilization and is between 50 and 300 Pa.

In one embodiment, the invention provides for the use of magnesium ascorbyl phosphate at a concentration of between 0.3 and 10 mg/g for retaining or improving the elasticity after sterilization of a composition comprising at least one hyaluronic acid or biologically acceptable salt thereof, alone or in a mixture.

In one embodiment of the use, the amount of hyaluronic acid or salt thereof, alone or in a mixture, in the composition is between 0.2% and 5% by weight, relative to the total weight of said composition.

In one embodiment of the use, the amount of hyaluronic acid or salt thereof, alone or in a mixture, in the composition is greater than or equal to 1% by weight, relative to the total weight of said composition.

In one embodiment of the use, the hyaluronic acid or salt thereof is crosslinked.

In one embodiment of the use, the hyaluronic acid or salt thereof has a degree of crosslinking of between 0.001 and 0.5.

In one embodiment of the use, the concentration of magnesium ascorbyl phosphate in the composition is between 0.3 and 10 mg/g, to improve the elasticity of said composition after sterilization.

In one embodiment of the use, the hyaluronic acid or salt thereof is noncrosslinked.

In one embodiment of the use, the concentration of magnesium ascorbyl phosphate in the composition is between 0.7 and 3 mg/g.

In one embodiment of the use, the concentration of magnesium ascorbyl phosphate in the composition is between 0.7 and 1 mg/g, to improve the elasticity of said composition after sterilization.

The invention likewise provides the use of magnesium ascorbyl phosphate as an agent for retaining or improving the elasticity after sterilization of a composition comprising at least one hyaluronic acid or biologically acceptable salt thereof, alone or in a mixture, the concentration of magnesium ascorbyl phosphate being between 0.3 and 10 mg/g, and the ratio [HA]/[MAP] by mass of the amount of hyaluronic acid or salt thereof [HA] to the amount of magnesium ascorbyl phosphate [MAP] being greater than or equal to 1.

The invention likewise provides a method for retaining or improving the elasticity after sterilization of a composition comprising at least one hyaluronic acid or biologically acceptable salt thereof, alone or in a mixture, which involves adding magnesium ascorbyl phosphate to the composition at a concentration of between 0.3 and 10 mg/g, the ratio [HA]/[MAP] by mass of the amount of hyaluronic acid or salt thereof [HA] to the amount of magnesium ascorbyl phosphate [MAP] being greater than or equal to 1.

In one embodiment of the method and/or of the use, the molecular mass Mw of the hyaluronic acid or salt thereof in the composition is between 0.01 and 5 MDa.

In one embodiment of the method and/or of the use, the amount of hyaluronic acid or salt thereof, alone or in a mixture, in the composition is between 0.2% and 5% by weight, relative to the total weight of said composition.

In one embodiment of the method and/or of the use, the amount of hyaluronic acid or salt thereof, alone or in a mixture, in the composition is greater than or equal to 1% by weight, relative to the total weight of said composition.

In one embodiment of the method and/or of the use, the composition comprises crosslinked hyaluronic acid or a salt thereof.

In one embodiment of the method and/or of the use, the hyaluronic acid or salt thereof in the composition has a degree of crosslinking of between 0.001 and 0.5.

In one embodiment of the method and/or of the use, the concentration of magnesium ascorbyl phosphate in the composition is between 0.3 and 10 mg/g, for improving the elasticity of said composition after sterilization.

In one embodiment of the method and/or of the use, the composition comprises noncrosslinked hyaluronic acid or a salt thereof.

In one embodiment of the method and/or of the use, the magnesium ascorbyl phosphate concentration in the composition is between 0.7 and 3 mg/g.

In one embodiment of the method and/or of the use, the concentration of magnesium ascorbyl phosphate in the composition is between 0.7 and 1 mg/g, for improving the elasticity of said composition after sterilization.

The invention likewise provides a method for producing a composition according to the invention.

In one embodiment, the method according to the invention comprises at least:
  a step of hydrating fibers of at least one hyaluronic acid or salt thereof, alone or in a mixture, to give a hydrogel,
  a step of mixing a solution of magnesium ascorbyl phosphate with the hydrogel obtained in the preceding step,
  a step of homogenizing; and
  a step of sterilizing.

In one embodiment, the method according to the invention has its hydrating step carried out at room temperature.

In one embodiment, the method according to the invention has its homogenizing step carried out at room temperature.

In one embodiment, the method according to the invention has the step of mixing a solution of magnesium ascorbyl phosphate with the hydrogel obtained in the hydrating step carried out at a temperature adapted to the production method. In one embodiment, it is carried out at room temperature.

In one embodiment, the sterilizing step is carried out by steam autoclaving.

In one embodiment, the sterilizing step is carried out by ethylene oxide.

In one embodiment, the sterilizing step is carried out by irradiation with gamma rays, γ.

In one embodiment, the method according to the invention has the sterilization by steam autoclaving carried out at a temperature of 121 to 134° C. for a time adapted to the temperature.

In one embodiment, the method according to the invention further comprises at least one step of packaging the homogenized mixture in syringes.

In one embodiment, the method according to the invention further comprises at least one step of packaging the homogenized mixture in single-dose vials.

In one embodiment, the method according to the invention further comprises at least one step of crosslinking.

In one embodiment, the method according to the invention has the crosslinking step situated between the hydrating step and the mixing step.

In one embodiment, the method according to the invention has the crosslinking step carried out by means of at least one crosslinking agent.

In one embodiment, the method according to the invention has the crosslinking agent being bifunctional or polyfunctional.

In one embodiment, the method according to the invention has the bifunctional or polyfunctional crosslinking agent selected from the group consisting of ethylene glycol diglycidyl ether, butanediol diglycidyl ether (BDDE), polyglycerol polyglycidyl ether, polyethylene glycol diglycidyl ether, polypropylene glycol diglycidyl ether, a bisepoxy or polyepoxy compound such as 1,2,3,4-diepoxybutane or 1,2,7,8-diepoxyoctane, a dialkyl sulfone, divinyl sulfone, formaldehyde, epichlorohydrin, or else glutaraldehyde, or carbodiimides such as, for example, 1-ethyl-3-[3-dimethylaminopropyl]carbodiimide hydrochloride (EDC).

In one embodiment, the method according to the invention has the bifunctional crosslinking agent being butanediol diglycidyl ether (BDDE) or 1,2,7,8-diepoxyoctane.

In one embodiment, the production method of the invention has the crosslinking step implemented in accordance with the techniques known to the person skilled in the art.

In one embodiment, the method according to the invention comprises, after the crosslinking step, at least one step of purifying and washing, which is carried out according to the techniques known to the person skilled in the art.

In one embodiment, the method according to the invention further comprises at least one step of mixing a solution of dimethyl sulfone with the hydrogel obtained in the hydrating step.

In one embodiment, the method according to the invention has the step of mixing a solution of dimethyl sulfone with the hydrogel obtained in the hydrating step situated before the homogenizing step.

In one embodiment, the method according to the invention has the step of mixing a solution of dimethyl sulfone with the hydrogel obtained in the hydrating step carried out at a temperature adapted to the production method. In one embodiment, it is carried out at room temperature.

In one embodiment, the method according to the invention further comprises at least one step of mixing a solution of at least one additional agent with the hydrogel obtained in the hydrating step.

In one embodiment, the method according to the invention has the step of mixing a solution of at least one additional agent with the hydrogel obtained in the hydrating step situated before the homogenizing step.

In one embodiment, the method according to the invention has the step of mixing a solution of at least one additional agent with the hydrogel obtained in the hydrating step carried out at a temperature adapted to the production method. In one embodiment, it is carried out at room temperature.

The invention provides for the use of a composition according to the invention to formulate a composition for filling in wrinkles.

The invention provides for the use of a composition according to the invention to formulate a viscosupplementation composition.

The intended applications are more particularly those applications that are commonly observed in the context of injectable viscoelastic products and polysaccharides that are used or potentially useful in the following pathologies or treatments:

esthetic facial injections: for filling in wrinkles, skin defects or volume defects (cheek bones, chin, lips);
  volumizing injections in the body: breast and buttock augmentation, G-spot augmentation, vaginoplasty, reconstruction of the vaginal labia, penis enlargement;
  treatment of osteoarthritis, injection into the joint to replace or supplement deficient synovial fluid;
  periurethral injection for the treatment of urinary incontinence due to sphincter insufficiency;
  post-surgical injection to prevent peritoneal adhesions in particular;
  injection following surgery for long-sightedness by scleral laser incisions;
  injection into the vitreous cavity;
  injection during cataract surgery;
  injection into genital parts.

More particularly, in esthetic surgery, according to its viscoelastic properties and persistence properties, the composition obtained by the method of the invention may be used:

for filling in fine, moderate or deep wrinkles, and may be injected using narrow-diameter needles (27 gauge, for example);
  as a volumizing product with injection by larger-diameter needles, from 22 to 26 gauge, for example, and longer needles (30 to 40 mm, for example); in this case, its cohesive nature will ensure that it is maintained at the site of the injection.

The composition according to the invention also finds major application in joint surgery and in dental surgery, for the filling in of periodontal pockets, for example.

These use examples are in no way limiting, and the composition according to the present invention is more broadly envisaged for:

filling in volumes;
  generating spaces within certain tissues, thereby promoting their optimum functioning;
  replacing deficient physiological fluids.

The invention also provides a kit comprising a composition according to the invention, packaged in syringes and sterilized after packaging.

The invention also provides a kit comprising a composition according to the invention, packaged in single-dose vials and sterilized after packaging.

The composition according to the invention also finds application in the cosmetic or pharmaceutical field.

More particularly in the cosmetic field, a composition according to the invention will be used as an active moisturizing ingredient in a cosmetic composition.

In the pharmaceutical field, a composition according to the invention will be used as a composition for hydrating eyes affected by ocular dryness, namely as an artificial tear.

In these cosmetic and/or pharmaceutical applications, the compositions may further comprise any cosmetically or pharmaceutically acceptable ingredient.

Figure 1:
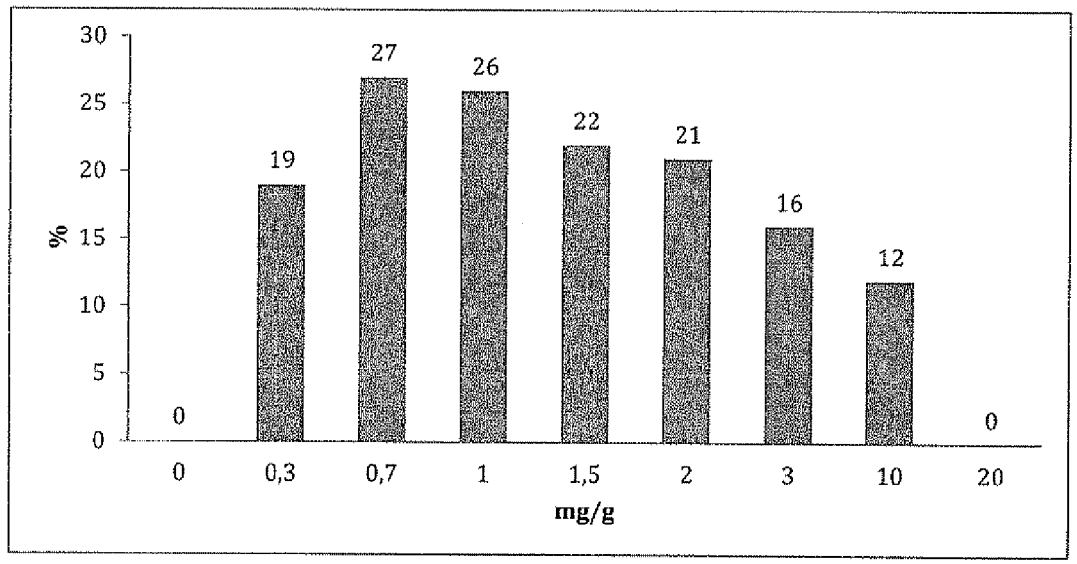
FIG. 1 is a diagram illustrating the percentage increase, on the ordinate in the diagram, in the elastic component G', as a function of the amount of magnesium ascorbyl phosphate in mg/g of composition, on the abscissa in the diagram, following sterilization by steam autoclaving of compositions comprising crosslinked hyaluronic acid and magnesium ascorbyl phosphate.

The characteristics of the composition according to the present invention and also methods for producing it, and the properties thereof, are illustrated in the examples below.

EXAMPLE 1

This example illustrates a composition according to the invention comprising noncrosslinked hyaluronic acid and magnesium ascorbyl phosphate.

Fibers of sodium hyaluronate (NaHA) of injectable grade (1 g; molecular mass: approximately 2.7 MDa) are weighed out into a container. An aqueous solution of phosphate buffer (32.3 g) is added, and the whole is homogenized for approximately 1 hour using a spatula, at room temperature and under an atmospheric pressure of 900 mmHg.

The noncrosslinked NaHA hydrogel thus obtained has an NaHA content of approximately 30 mg/g.

Magnesium ascorbyl phosphate (MAP) (60 mg or $2.4 \times 10^{-4}$ mol) is dissolved in a phosphate buffer solution (19.94 g) to give an aqueous solution of magnesium ascorbyl phosphate with a content of 3 mg/g.

The NaHA hydrogel obtained in the preceding step is diluted by adding the pre-prepared aqueous solution of magnesium ascorbyl phosphate. The resulting composition is then homogenized.

This gives a composition comprising noncrosslinked NaHA in an amount of 20 mg/g and MAP in an amount of 1 mg/g; the ratio [HA]/[MAP] by mass is 20.

The composition thus obtained is packaged in syringes which are sterilized by steam autoclaving (T=121° C., 10 min).

EXAMPLE 2

This example illustrates a composition example according to the invention comprising crosslinked hyaluronic acid and magnesium ascorbyl phosphate.

The composition comprising crosslinked hyaluronic acid is obtained by the crosslinking procedure described in WO 2009/071697 (example 1, first part) to VIVACY, starting from fibers of sodium hyaluronate (NaHA) (1 g; molecular mass: approximately 2.7 MDa) and butanediol diglycidyl ether (BDDE) (54 mg). The resulting composition contains approximately 30 mg/g of crosslinked NaHA with a degree of crosslinking X of approximately 0.12.

An aqueous solution of magnesium ascorbyl phosphate with a content of 3 mg/g is prepared as in example 1.

The crosslinked NaHA hydrogel obtained in the preceding step is diluted by adding the pre-prepared aqueous solution of magnesium ascorbyl phosphate. The resulting composition is then homogenized.

This gives a composition comprising crosslinked NaHA in an amount of 20 mg/g and magnesium ascorbyl phosphate in an amount of 1 mg/g; the ratio [HA]/[MAP] by mass is 20.

The composition thus obtained is packaged in syringes which are sterilized by steam autoclaving (T=121° C., 10 min).

EXAMPLE 3

This example illustrates a composition example according to the invention, comprising crosslinked hyaluronic acid, magnesium ascorbyl phosphate, and lidocaine.

A composition comprising crosslinked NaHA is prepared by the procedure described in example 2, starting from an NaHA hydrogel with a content of 30 mg/g and from magnesium ascorbyl phosphate with a content of 10 mg/g.

The addition of a lidocaine solution with a content of 13 mg/g to the composition obtained above is made by the procedure described in WO 2009/024670 to ANTEIS or by the procedure described in patent applications U.S. 61/791,977 or FR 13/52971 to VIVACY.

The resulting composition comprises crosslinked hyaluronic acid in an amount of 20 mg/g, lidocaine in an amount of 3 mg/g, and magnesium ascorbyl phosphate in an amount of 1 mg/g; the ratio [HA]/[MAP] by mass is 20.

The resulting composition is packaged in syringes which are sterilized by steam autoclaving (T=121° C., 10 min).

EXAMPLE 4

This example illustrates a composition example according to the invention, comprising noncrosslinked hyaluronic acid, magnesium ascorbyl phosphate, and dimethyl sulfone.

The composition comprising noncrosslinked hyaluronic acid and magnesium ascorbyl phosphate is prepared by the procedure of example 1, starting from a hydrogel of hyaluronic acid with a content of 30 mg/g and from a magnesium ascorbyl phosphate solution with a content of 10 mg/g.

A solution of dimethyl sulfone with a content of 4.3 mg/g is also added to the composition obtained above.

The resulting composition is then homogenized.

This gives a composition which comprises noncrosslinked hyaluronic acid in an amount of 20 mg/g, dimethyl sulfone in an amount of 1 mg/g, and magnesium ascorbyl phosphate in an amount of 1 mg/g; the ratio [HA]/[MAP] by mass is 20.

The resulting composition is packaged in syringes which are sterilized by steam autoclaving (T=121° C., 10 min).

EXAMPLE 5

This example illustrates a composition example according to the invention, comprising crosslinked hyaluronic acid, magnesium ascorbyl phosphate, and dimethyl sulfone.

A composition comprising crosslinked NaHA is prepared by the procedure described in example 2, starting from an NaHA hydrogel with a content of 30 mg/g and from magnesium ascorbyl phosphate with a content of 10 mg/g.

A solution of dimethyl sulfone with a content of 4.3 mg/g is also added to the composition obtained above.

The resulting composition is then homogenized.

This gives a composition which comprises crosslinked hyaluronic acid in an amount of 20 mg/g, dimethyl sulfone in an amount of 1 mg/g, and magnesium ascorbyl phosphate in an amount of 1 mg/g; the ratio [HA]/[MAP] by mass is 20.

The resulting composition is packaged in syringes which are sterilized by steam autoclaving (T=121° C., 10 min).

EXAMPLE 6

This example illustrates a composition example comprising noncrosslinked hyaluronic acid, magnesium ascorbyl phosphate, and mannitol.

A composition comprising noncrosslinked NaHA is prepared by the procedure described in example 1, starting from an NaHA hydrogel with a content of 30 mg/g and from magnesium ascorbyl phosphate with a content of 10 mg/g.

A solution of mannitol with a content of 4.3 mg/g is also added to the composition obtained above.

The resulting composition is then homogenized.

This gives a composition which comprises noncrosslinked hyaluronic acid in an amount of 20 mg/g, magnesium ascorbyl phosphate in an amount of 1 mg/g and mannitol in an amount of 1 mg/g; the ratio [HA]/[MAP] by mass is 20.

The resulting composition is packaged in syringes which are sterilized by steam autoclaving (T=121° C., 10 min).

EXAMPLE 7

This example illustrates a composition example comprising crosslinked hyaluronic acid, magnesium ascorbyl phosphate, and mannitol.

A composition comprising crosslinked NaHA is prepared by the procedure described in example 2, starting from an NaHA hydrogel with a content of 30 mg/g and from magnesium ascorbyl phosphate with a content of 10 mg/g.

A solution of mannitol with a content of 4.3 mg/g is also added to the composition obtained above.

The resulting composition is then homogenized.

This gives a composition which comprises crosslinked hyaluronic acid in an amount of 20 mg/g, magnesium ascorbyl phosphate in an amount of 1 mg/g and mannitol in an amount of 1 mg/g; the ratio [HA]/[MAP] by mass is 20.

The resulting composition is packaged in syringes which are sterilized by steam autoclaving (T=121° C., 10 min).

EXAMPLE 8

This example illustrates a composition example comprising crosslinked hyaluronic acid and sodium ascorbyl phosphate (SAP).

The composition comprising crosslinked hyaluronic acid and sodium ascorbyl phosphate is prepared by the procedure of example 2, starting from a hyaluronic acid gel with a content of 30 mg/g and from sodium ascorbyl phosphate with a content of 3 mg/g.

The resulting composition comprises crosslinked hyaluronic acid in an amount of 20 mg/g and sodium ascorbyl phosphate in an amount of 1 mg/g; the ratio [HA]/[SAP] by mass is 20.

The resulting composition is packaged in syringes which are sterilized by steam autoclaving (T=121° C., 10 min).

EXAMPLE 9

This counterexample illustrates a composition example comprising noncrosslinked hyaluronic acid and mannitol.

The composition comprising noncrosslinked hyaluronic acid and mannitol (MAN) is prepared by the procedure of example 1, starting from a hyaluronic acid hydrogel with a content of 30 mg/g and from a solution of mannitol with a content of 3 mg/g.

The resulting composition comprises noncrosslinked hyaluronic acid in an amount of 20 mg/g and mannitol in an amount of 1 mg/g; the ratio [HA]/[MAN] by mass is 20.

The resulting composition is packaged in syringes which are sterilized by steam autoclaving (T=121° C., 10 min).

EXAMPLE 10

This counterexample illustrates a composition example comprising crosslinked hyaluronic acid and mannitol.

A composition comprising crosslinked NaHA is prepared by the procedure described in example 2, starting from an NaHA hydrogel with a content of 30 mg/g and from mannitol with a content of 3 mg/g.

The resulting composition comprises crosslinked hyaluronic acid in an amount of 20 mg/g and mannitol in an amount of 1 mg/g; the ratio [HA]/[MAN] by mass is 20.

The resulting composition is packaged in syringes which are sterilized by steam autoclaving (T=121° C., 10 min).

EXAMPLE 11

Characterization of the rheological properties before and after sterilization by steam autoclaving of the compositions comprising crosslinked hyaluronic acid that are exemplified above.

The elastic components G' of the compositions comprising crosslinked hyaluronic acid, before and after sterilization by steam autoclaving, were measured on a TA Instrument AR 2000 Ex rheometer, in oscillation at 25° C., with the values for the elastic component G' being related to a frequency of 1 Hz.

For all of the measurements, a reference composition is formulated, by replacing the aqueous solution of magnesium ascorbyl phosphate with an equivalent quantity of aqueous phosphate buffer solution.

The percentage improvement in the elastic component G' is defined as follows:

$$\% \text{ improvement in } G' = \frac{Y - Y'}{Y} \cdot 100$$

where Y=percentage loss in elastic component G' on sterilization of the reference composition
and Y'=percentage loss in elastic component G' on sterilization of the composition tested.

Eight compositions comprising crosslinked hyaluronic acid and magnesium ascorbyl phosphate in an amount of between 0.3 and 20 mg/g in the composition are prepared by the procedure described in example 2.

Three compositions comprising crosslinked hyaluronic acid and mannitol in an amount of between 1 and 10 mg/g in the composition are prepared by the procedure described in example 10.

Two compositions comprising crosslinked hyaluronic acid and sodium ascorbyl phosphate in an amount of between 1 and 5 mg/g in the composition are prepared according to example 8.

A reference composition comprising crosslinked hyaluronic acid is prepared by the procedure described in example 2. The aqueous solution of magnesium ascorbyl phosphate is replaced with an equivalent amount of an aqueous phosphate buffer solution.

The elastic components of the compositions tested are measured before and after sterilization and the percentage improvements in the elastic component G' are calculated, with the results obtained being presented in table 1 below:

TABLE 1

| Test | [MAP] (mg/g) | Ratio [HA]/[MAP] | [MAN] (mg/g) | [SAP] (mg/g) | % improvement in elastic component G' relative to reference composition | Elastic component G' (Pa) of sterile gels |
| --- | --- | --- | --- | --- | --- | --- |
| 1 | 0 | n/a | 0 | 0 | 0 | 144 |
| 2 | 0.3 | 67 | 0 | 0 | 19 | 180 |
| 3 | 0.7 | 29 | 0 | 0 | 27 | 192 |
| 4 | 1 | 20 | 0 | 0 | 26 | 191 |
| 5 | 1.5 | 13 | 0 | 0 | 22 | 185 |
| 6 | 2 | 10 | 0 | 0 | 21 | 182 |
| 7 | 3 | 7 | 0 | 0 | 16 | 172 |
| 8 | 10 | 2 | 0 | 0 | 12 | 160 |
| 9 | 20 | 1 | 0 | 0 | 0 | 142 |
| 10 | 0 | n/a | 1 | 0 | 15 | 163 |
| 11 | 0 | n/a | 5 | 0 | 25 | 182 |
| 12 | 0 | n/a | 10 | 0 | 29 | 188 |
| 13 | 0 | n/a | 0 | 1 | −12 | 105 |
| 14 | 0 | n/a | 0 | 5 | −26 | 76 | n/a: not applicable

The results obtained above for the compositions comprising MAP are also illustrated by FIG. 1, which is a diagram representing the percentage increase in the elastic component G' as a function of the magnesium ascorbyl phosphate content after sterilization by steam autoclaving of compositions comprising crosslinked hyaluronic acid and magnesium ascorbyl phosphate.

For the compositions comprising crosslinked hyaluronic acid and magnesium ascorbyl phosphate in an amount of between 0.3 and 20 mg/g it is observed that the elastic component G' is improved, relative to the reference composition, when the amount of magnesium ascorbyl phosphate is between 0.3 and 10 mg/g, with a sharp drop when this amount is greater than 10 mg/g.

These results contradict the results obtained for the compositions comprising crosslinked hyaluronic acid and mannitol, which show that, the more the mannitol content of the composition is increased, the more the elastic component G' is improved relative to the reference composition.

They also contradict the results obtained for the compositions comprising crosslinked hyaluronic acid and SAP, for which the elastic component G' is reduced at the two concentrations tested.

EXAMPLE 12

Characterization of the rheological properties before and after sterilization by steam autoclaving of compositions comprising noncrosslinked hyaluronic acid.

The compositions comprising noncrosslinked hyaluronic acid are characterized by their viscosity $\eta$.

The viscosity $\eta$ of the compositions is measured on a TA Instruments AR 2000 Ex rheometer, in imposed stress at 25° C. The viscosity value is related to a stress of 0.02 s-1.

Six compositions comprising noncrosslinked hyaluronic acid and magnesium ascorbyl phosphate in an amount of between 0.3 and 3 mg/g in the composition are prepared by the procedure described in example 1.

A reference composition comprising noncrosslinked hyaluronic acid is prepared by the procedure described in example 1. The aqueous solution of magnesium ascorbyl phosphate described in the procedure for example 1 is replaced with an equivalent amount of an aqueous phosphate buffer solution.

The percentage improvement in the viscosity $\eta$ is defined as follows:

$$\% \text{ improvement in the viscosity } \eta = \frac{Z - Z'}{Z} \cdot 100$$

where Z=percentage loss in viscosity $\eta$ on sterilization of the reference composition
and Z'=percentage loss in viscosity $\eta$ on sterilization of the composition tested.

The viscosities of the compositions tested are measured before and after sterilization and the percentage improvements in the viscosity are calculated, with the results obtained being presented in table 2 below:

TABLE 2

| Test | [MAP] (mg/g) | % improvement in viscosity relative to reference composition |
|---|---|---|
| 15 | 0 | 0 |
| 16 | 0.3 | −4 |
| 17 | 0.7 | 0 |
| 18 | 1 | 0 |

TABLE 2-continued

| Test | [MAP] (mg/g) | % improvement in viscosity relative to reference composition |
|---|---|---|
| 19 | 1.5 | −4 |
| 20 | 2 | −7 |
| 21 | 3 | −12 |

Figure 2:
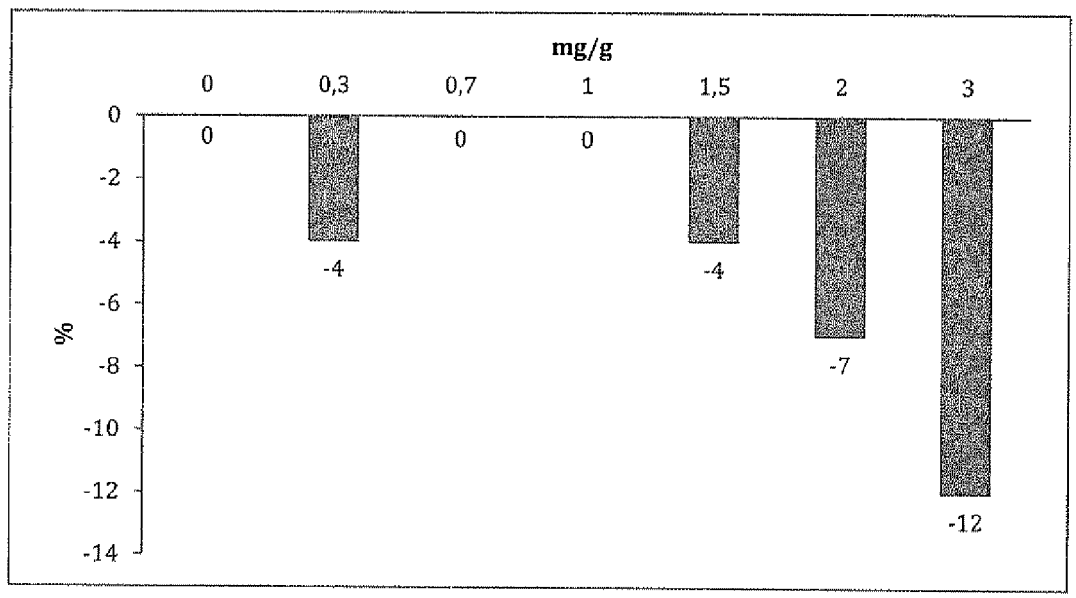
FIG. 2 is a diagram illustrating the percentage increase, on the ordinate in the diagram, in the viscosity $\eta$, as a function of the amount of magnesium ascorbyl phosphate in mg/g of composition, on the abscissa in the diagram, following sterilization by steam autoclaving of compositions comprising noncrosslinked hyaluronic acid and magnesium ascorbyl phosphate.

The results obtained above are also illustrated in FIG. 2, which is a diagram representing the percentage increase in the viscosity $\eta$ as a function of the magnesium ascorbyl phosphate content after sterilization by steam autoclaving of compositions comprising noncrosslinked hyaluronic acid and magnesium ascorbyl phosphate.

A retention of the viscosity is observed for the compositions according to the invention having a magnesium ascorbyl phosphate content of between 0.7 and 1 mg/g, relative to the reference composition.

EXAMPLE 12BIS A)

A similar test was carried out with rheological monitoring of the elastic component G'.

Seven compositions comprising noncrosslinked hyaluronic acid and magnesium ascorbyl phosphate in an amount of between 0.3 and 1.25 mg/g in the composition are prepared by the procedure described in example 1 (the molecular mass of sodium hyaluronate is approximately 2.7 MDa).

A reference composition comprising noncrosslinked hyaluronic acid is prepared by the procedure described in example 1. The aqueous solution of magnesium ascorbyl phosphate described in the procedure for example 1 is replaced with an equivalent amount of an aqueous phosphate buffer solution.

The elastic components G' of the compositions tested are measured before and after sterilization and the percentage improvements in the elastic component G' are calculated, with the results obtained being presented in table 3 below:

TABLE 3

| Test | [MAP] (mg/g) | % improvement in elastic component G' relative to reference composition | Elastic component G' (Pa) |
|---|---|---|---|
| 15 | 0 | 0 | 134 |
| 16 | 0.3 | 11 | 169 |
| 40 | 0.5 | 12 | 172 |
| 17 | 0.7 | 7 | 161 |
| 41 | 0.85 | 5 | 148 |
| 18 | 1 | 4 | 153 |
| 42 | 1.25 | 0 | 132 |

An improvement in elasticity is observed for the compositions according to the invention having a magnesium ascorbyl phosphate content of between 0.3 and 1 mg/g relative to the reference composition, and also a retention of elasticity for a magnesium ascorbyl phosphate content of 1.25 mg/g.

EXAMPLE 12BIS B)

A test identical to test 12bis a) described above was carried out with compositions comprising noncrosslinked sodium hyaluronate with a molecular mass of approximately 1.4 MDa, and the elastic component G' was monitored rheologically. The compositions are prepared by the procedure described in example 1, with substitution of the 2.7 MDa molecular mass sodium hyaluronate by 1.4 MDa molecular mass sodium hyaluronate.

The elastic components G' of the compositions tested are measured before and after sterilization and the percentage improvements in the elastic component G' are calculated, with the results obtained being presented in table 4 below:

TABLE 4

| Test | [MAP] (mg/g) | % improvement in elastic component G' relative to reference composition | Elastic component G' (Pa) |
|---|---|---|---|
| 43 | 0 | 0 | 7 |
| 44 | 0.7 | 20 | 10 |
| 45 | 1 | 16 | 9 |
| 46 | 3 | 0 | 7 |

An improvement in elasticity is observed for the compositions according to the invention having a magnesium ascorbyl phosphate content of between 0.7 and 1 mg/g relative to the reference composition, and also a retention of the elasticity for a magnesium ascorbyl phosphate content of 3 mg/g.

EXAMPLE 13

Characterization of the rheological properties before and after sterilization by steam autoclaving of compositions comprising crosslinked hyaluronic acid, magnesium ascorbyl phosphate, and an additional agent.

The rheological properties before and after sterilization by steam autoclaving of compositions comprising crosslinked hyaluronic acid, magnesium ascorbyl phosphate, and an additional agent are measured and the percentage improvements in the elastic component G' are calculated, according to the protocol described in example 11.

Four compositions comprising crosslinked hyaluronic acid, magnesium ascorbyl phosphate in an amount of 1 mg/g, and an additional agent in an amount of 1 mg/g in the composition are prepared by the procedure described in example 7. The additional agents exemplified are mannitol (MAN), sorbitol (SOR), the water-soluble salt of potassium sucrose octasulfate (KSOS), and lidocaine hydrochloride (LIDO).

A composition comprising crosslinked hyaluronic acid and magnesium ascorbyl phosphate in an amount of 1 mg/g is prepared by the procedure described in example 2.

A reference composition comprising crosslinked hyaluronic acid is prepared by the procedure described in example 2. The aqueous solution of magnesium ascorbyl phosphate is replaced with an equivalent amount of an aqueous phosphate buffer solution.

The elastic components of the compositions tested are measured before and after sterilization and the percentage improvements in the elastic component G' are calculated, with the results obtained being presented in table 5 below:

TABLE 5

| Test | [MAP] (mg/g) | Additional agent in an amount of 1 mg/g | % improvement in elastic component G' relative to reference composition | Elastic component G' (Pa) of sterile gels |
|---|---|---|---|---|
| 22 | 0 | 0 | 0 | 138 |
| 23 | 1 | 0 | 31 | 196 |
| 24 | 1 | MAN | 31 | 197 |
| 25 | 1 | SOR | 29 | 197 |
| 26 | 1 | KSOS | 29 | 195 |
| 27 | 1 | LIDO | 8 | 153 |

It is found that the improvement in rheological properties that is observed in example 11 for the compositions comprising hyaluronic acid and magnesium ascorbyl phosphate is retained in the presence of all of the additional agents. Only the addition of lidocaine hydrochloride entails a significant reduction in this improvement.

EXAMPLE 13BIS

Characterization of the rheological properties before and after sterilization by steam autoclaving of compositions comprising crosslinked hyaluronic acid, magnesium ascorbyl phosphate, and lidocaine at 3 mg/g.

The elastic components of the compositions tested are measured before and after sterilization and the percentage improvements in the elastic component G' are calculated, with the results obtained being presented in table 6 below:

TABLE 6

| Test | [MAP] (mg/g) | [LIDO] (mg/g) | % improvement in elastic component G' relative to reference composition | Elastic component G' (Pa) of sterile gels |
|---|---|---|---|---|
| 47 | 0 | 0 | 0 | 109 |
| 48 | 1 | 0 | 30 | 144 |
| 49 | 0 | 3 | −7 | 103 |
| 50 | 1 | 3 | −5 | 104 |
| 51 | 3 | 3 | 22 | 138 |
| 52 | 10 | 3 | 9 | 120 |

The addition of lidocaine alone is found to entail a reduction in the elastic component G' of the composition after sterilization. The addition of MAP at 1 mg/g is unable to counter the effect of the lidocaine on the elasticity of the composition. However, the addition of MAP at 3 and 10 mg/g does improve the elasticity of the composition in the presence of lidocaine. These results are unexpected and are contrary to the teachings and effects described in the prior art and especially abovementioned WO2012/104419 to Q-MED.

EXAMPLE 14

Characterization of the rheological properties before and after sterilization by steam autoclaving of compositions comprising noncrosslinked hyaluronic acid, magnesium ascorbyl phosphate, and an additional agent.

The rheological properties before and after sterilization by steam autoclaving of compositions comprising noncrosslinked hyaluronic acid, magnesium ascorbyl phosphate, and an additional agent are measured and the percentage improvements in viscosity are calculated, according to the protocol described in example 12.

Three compositions comprising noncrosslinked hyaluronic acid, magnesium ascorbyl phosphate in an amount of 1 mg/g, and an additional agent in an amount of 1 mg/g in the composition are prepared by the procedure described in example 6. The additional agents exemplified are mannitol (MAN), sorbitol (SOR), and the water-soluble salt of potassium sucrose octasulfate (KSOS).

A composition comprising noncrosslinked hyaluronic acid and magnesium ascorbyl phosphate in an amount of 1 mg/g is prepared by the procedure described in example 1.

A reference composition comprising noncrosslinked hyaluronic acid is prepared by the procedure described in example 1. The aqueous solution of magnesium ascorbyl phosphate described in the procedure for example 1 is replaced with an equivalent amount of an aqueous phosphate buffer solution.

The viscosities of the compositions tested are measured before and after sterilization and the percentage improvements in the viscosity are calculated, with the results obtained being presented in table 7 below:

TABLE 7

| Test | [MAP] (mg/g) | Additional agent in an amount of 1 mg/g | % improvement in viscosity η, relative to reference composition |
|---|---|---|---|
| 28 | 0 | 0 | 0 |
| 29 | 1 | 0 | 0 |
| 30 | 1 | MAN | 0 |
| 31 | 1 | SOR | 0 |
| 32 | 1 | KSOS | 0 |

A retention of the viscosity is observed for all of the compositions.

EXAMPLE 15

Characterization of the rheological properties before and after sterilization by steam autoclaving of compositions comprising crosslinked hyaluronic acid, magnesium ascorbyl phosphate, and dimethyl sulfone (DMS).

The rheological properties before and after sterilization by steam autoclaving of compositions comprising crosslinked hyaluronic acid, magnesium ascorbyl phosphate, and dimethyl sulfone (DMS) are measured and the percentage improvements in the elastic component G' are calculated, according to the protocol described in example 11.

Two compositions comprising crosslinked hyaluronic acid, magnesium ascorbyl phosphate in an amount of 1 mg/g in the composition, and dimethyl sulfone in an amount of between 1 and 10 mg/g in the composition are prepared by the procedure described in example 5.

One composition comprising crosslinked hyaluronic acid and magnesium ascorbyl phosphate in an amount of 1 mg/g is prepared by the procedure described in example 2.

A reference composition comprising crosslinked hyaluronic acid is prepared by the procedure described in example 2. The aqueous solution of magnesium ascorbyl phosphate is replaced with an equivalent amount of an aqueous phosphate buffer solution.

The elastic components of the compositions tested are measured before and after sterilization and the percentage improvements in the elastic component G' are calculated, with the results obtained being presented in table 8 below:

TABLE 8

| Test | [MAP] (mg/g) | [DMS] (mg/g) | % improvement in elastic component G' relative to reference composition | Elastic component G' (Pa) of sterile gels |
|---|---|---|---|---|
| 33 | 0 | 0 | 0 | 185 |
| 34 | 1 | 0 | 29 | 243 |
| 35 | 1 | 1 | 30 | 242 |
| 36 | 1 | 10 | 29 | 246 |

It is found that the improvement in rheological properties observed in example 11 for the compositions comprising hyaluronic acid and magnesium ascorbyl phosphate is retained in the presence of DMS in an amount of between 1 and 10 mg/g.

EXAMPLE 16

Characterization of the rheological properties before and after sterilization by steam autoclaving of compositions comprising noncrosslinked hyaluronic acid, magnesium ascorbyl phosphate, and dimethyl sulfone (DMS).

The rheological properties before and after sterilization by steam autoclaving of compositions comprising noncrosslinked hyaluronic acid, magnesium ascorbyl phosphate, and dimethyl sulfone (DMS) are measured and the percentage improvements in the viscosity are calculated, according to the protocol described in example 12.

The composition comprising noncrosslinked hyaluronic acid, magnesium ascorbyl phosphate in an amount of 1 mg/g in the composition, and dimethyl sulfone in an amount of 1 mg/g in the composition according to the invention is prepared and sterilized by the procedure described in example 4 and is characterized by rheology according to example 12.

One composition comprising noncrosslinked hyaluronic acid and magnesium ascorbyl phosphate in an amount of 1 mg/g is prepared by the procedure described in example 1.

A reference composition comprising noncrosslinked hyaluronic acid is prepared by the procedure described in example 1. The aqueous solution of magnesium ascorbyl phosphate described in the procedure for example 1 is replaced with an equivalent amount of an aqueous phosphate buffer solution.

The viscosities of the compositions tested are measured before and after sterilization and the percentage improvements in the viscosity are calculated, with the results obtained being presented in table 9 below:

TABLE 9

| Test | [MAP] (mg/g) | [DMS] (mg/g) | % improvement in viscosity η relative to reference composition |
|---|---|---|---|
| 37 | 0 | 0 | 0 |
| 38 | 1 | 0 | 0 |
| 39 | 1 | 1 | 0 |

A retention in viscosity is found for the composition comprising noncrosslinked hyaluronic acid, magnesium ascorbyl phosphate in an amount of 1 mg/g, and dimethyl sulfone in an amount of 1 mg/g.

EXAMPLE 17

Comparison with the compositions described in the prior art.

In international patent application WO 2011/086458 to ALLERGAN, example 4 describes a composition comprising crosslinked hyaluronic acid and magnesium ascorbyl phosphate in amounts of between 0.6 and 2% by weight, relative to the total weight of the composition. According to the patentee, these compositions are said not to be stable, since the Δ Tan δ 1 Hz values of said compositions are greater than 0.1.

The Δ Tan δ 1 Hz values of the compositions comprising crosslinked hyaluronic acid and magnesium ascorbyl phosphate in amounts respectively of 0.6% and 1% are not defined.

Only the Δ Tan δ 1 Hz value of the composition comprising crosslinked hyaluronic acid and magnesium ascorbyl phosphate in an amount of 2% is defined, and is 0.344, a value greater than 0.1.

WO 2011/086458 also teaches that the greater the amount of magnesium ascorbyl phosphate in the composition, the more the Δ Tan δ 1 Hz value in said composition tends to reduce and tends to approach the value of 0.1.

As in the patent application cited above, the compositions studied earlier are characterized by their Δ Tan δ 1 Hz, which is the difference between the Tan δ 1 Hz of the composition tested and the Tan δ 1 Hz of the reference composition, with Tan δ 1 Hz being the ratio of the viscous component G" to the elastic component G'.

The Δ Tan δ 1 Hz values of the compositions tested, relative to the reference composition, are presented in table 10 below:

TABLE 10

| Test | [MAP] (mg/g) | [MAN] (mg/g) | [SAP] (mg/g) | Δ Tan δ 1 Hz |
|---|---|---|---|---|
| 1 | 0 | 0 | 0 | 0 |
| 2 | 0.3 | 0 | 0 | −0.0135 |
| 3 | 0.7 | 0 | 0 | −0.0145 |
| 4 | 1 | 0 | 0 | −0.0140 |
| 5 | 1.5 | 0 | 0 | −0.0128 |
| 6 | 2 | 0 | 0 | −0.0136 |
| 7 | 3 | 0 | 0 | −0.0084 |
| 8 | 10 | 0 | 0 | −0.0008 |
| 9 | 20 | 0 | 0 | 0.0240 |
| 10 | 0 | 1 | 0 | −0.0131 |
| 11 | 0 | 5 | 0 | −0.0196 |
| 12 | 0 | 10 | 0 | −0.0210 |
| 13 | 0 | 0 | 1 | 0.0203 |
| 14 | 0 | 0 | 5 | 0.0771 |

It is found that the Δ Tan δ 1 Hz values of the compositions comprising crosslinked hyaluronic acid and magnesium ascorbyl phosphate in an amount of between 0.3 and 20 mg/g are less than 0.1.

It can also be seen that the Δ Tan δ 1 Hz values of the compositions comprising crosslinked hyaluronic acid and mannitol in an amount of between 1 and 10 mg/g are lower than 0.1, and also the Δ Tan δ 1 Hz values of the compositions comprising crosslinked hyaluronic acid and SAP in an amount of between 1 and 5 mg/g.

In conclusion, the results obtained for the compositions comprising crosslinked hyaluronic acid and magnesium ascorbyl phosphate of between 0.3 and 20 mg/g are in contradiction relative to the teaching of WO 2011/086458, since, with amounts of magnesium ascorbyl phosphate that are equivalent to or less than that in WO 2011/086458 in the compositions according to the invention, the Δ Tan δ 1 Hz values therefore are less than 0.1.

The same determinations of Δ Tan δ 1 Hz were carried out on compositions comprising crosslinked hyaluronic acid, magnesium ascorbyl phosphate, and an additional agent, and the values obtained are presented in table 11 below:

TABLE 11

| Test | [MAP] (mg/g) | Additional agent in an amount of 1 mg/g | Δ Tan δ 1 Hz |
|---|---|---|---|
| 22 | 0 | 0 | 0 |
| 23 | 1 | 0 | −0.0197 |
| 24 | 1 | MAN | −0.0191 |
| 25 | 1 | SOR | −0.0181 |
| 26 | 1 | KSOS | −0.0142 |
| 27 | 1 | LIDO | −0.0068 |

It is found, as before, that the Δ Tan δ 1 Hz values after sterilization by steam autoclaving are less than 0.1.

The same determinations of Δ Tan δ 1 Hz were carried out on compositions comprising crosslinked hyaluronic acid, magnesium ascorbyl phosphate, and dimethyl sulfone (DMS), and the values obtained are presented in table 12 below:

TABLE 12

| Test | [MAP] (mg/g) | [DMS] (mg/g) | Δ Tan δ 1 Hz |
|---|---|---|---|
| 33 | 0 | 0 | 0 |
| 34 | 1 | 0 | −0.0050 |
| 35 | 1 | 1 | −0.0061 |
| 36 | 1 | 10 | −0.0064 |

It is found again that the Δ Tan δ 1 Hz values are less than 0.1.

What is claimed is:

1. A sterilized composition comprising at least one crosslinked hyaluronic acid or biologically acceptable salt thereof, alone or in a mixture, and magnesium ascorbyl phosphate, in a ratio [HA]/[MAP] by mass of the amount of hyaluronic acid or salt thereof [HA] to the amount of magnesium ascorbyl phosphate [MAP] of greater than or equal to 1, the amount of magnesium ascorbyl phosphate being between 0.001% and 1% by weight, relative to the total weight of said composition, wherein the crosslinked hyaluronic acid or salt thereof has a degree of crosslinking ranging from 0.1 to 0.2, with an elastic component G' which is retained or increased after sterilization, relative to a same composition not comprising magnesium ascorbyl phosphate, and is between 5 and 400 Pa.

2. The composition as claimed in claim 1, wherein the amount of magnesium ascorbyl phosphate is between 0.03% and 1% by weight, relative to the total weight of said composition.

3. The composition as claimed in claim 1, wherein the amount of magnesium ascorbyl phosphate is between 0.05% and 0.15% by weight, relative to the total weight of said composition.

4. The composition as claimed in claim 1, wherein the amount of magnesium ascorbyl phosphate is between 0.03% and 0.1% by weight, relative to the total weight of said composition.

5. The composition as claimed in claim 1, wherein the amount of magnesium ascorbyl phosphate is between 0.07% and 0.1% by weight, relative to the total weight of said composition.

6. The composition as claimed in claim 1, further comprising dimethyl sulfone.

7. The composition as claimed in claim 6, wherein the amount of dimethyl sulfone is between 0.001% and 5% by weight, relative to the total weight of said composition.

8. The composition as claimed in claim 6, wherein the amount of dimethyl sulfone is between 0.1% and 1% by weight, relative to the total weight of said composition.

9. The composition as claimed in claim 1, wherein the molecular mass Mw of the hyaluronic acid or salt thereof is between 0.01 and 5 MDa.

10. The composition as claimed in claim 1, wherein the amount of hyaluronic acid or salt thereof, alone or in a mixture, is between 0.2% and 5% by weight, relative to the total weight of said composition.

11. The composition as claimed in claim 1, wherein the amount of hyaluronic acid or salt thereof, alone or in a mixture, is greater than or equal to 1% by weight, relative to the total weight of said composition.

12. The composition as claimed in claim 1, further comprising at least one noncrosslinked hyaluronic acid or salt thereof.

13. The composition as claimed in claim 1, said composition further comprising at least one additional agent.

14. The composition as claimed in claim 13, wherein the additional agent is selected from antioxidants and local anesthetics, alone or in a mixture.

15. The composition as claimed in claim 14, wherein the local anesthetics are selected from the group consisting of lidocaine, procaine, mepivacaine, ropivacaine, bupivacaine, or pharmaceutically acceptable salts thereof.

16. The composition as claimed in claim 14, wherein the antioxidants are selected from polyols.

17. The composition as claimed in claim 1, wherein the elastic component G' is increased after sterilization, relative to a same composition not comprising magnesium ascorbyl phosphate.

18. A composition for filling in wrinkles comprising the composition as claimed in claim 1.

19. A composition for viscosupplementation comprising the composition as claimed in claim 1.

20. A kit comprising a composition as claimed in claim 1, packaged in sterile syringes.

21. A method for producing a composition as claimed in claim 1, wherein said production method comprises at least:
    hydrating fibers of at least one hyaluronic acid or salt thereof, alone or in a mixture, to give a hydrogel,
    mixing a solution of magnesium ascorbyl phosphate with the hydrogel obtained in the preceding step,
    homogenizing; and
    sterilizing.

22. A method for producing a composition as claimed in claim 15, wherein said method further comprises crosslinking.

23. The production method as claimed in claim 15, wherein said method further comprises mixing a solution of dimethyl sulfone with the hydrogel.

* * * * *